United States Patent
Bhatnagar et al.

(10) Patent No.: US 7,329,513 B2
(45) Date of Patent: Feb. 12, 2008

(54) HIGH LEVEL CONSTITUTIVE PRODUCTION OF ANTHRAX PROTECTIVE ANTIGEN

(75) Inventors: Rakesh Bhatnagar, Centre of Biotechnology, Jawaharlal, Nehru University, New Delhi, 110 067 (IN); Waheed Sayed Mohsin, New Delhi (IN); Vibha Chauhan, New Delhi (IN)

(73) Assignee: Rakesh Bhatnagar, New Delhi (IN)

( * ) Notice: Subject to any disclaimer, the term of this patent is extended or adjusted under 35 U.S.C. 154(b) by 0 days.

(21) Appl. No.: 10/494,680

(22) PCT Filed: Dec. 7, 2001

(86) PCT No.: PCT/IN01/00215

§ 371 (c)(1),
(2), (4) Date: Nov. 2, 2004

(87) PCT Pub. No.: WO03/040179

PCT Pub. Date: May 15, 2003

(65) Prior Publication Data

US 2005/0054038 A1 Mar. 10, 2005

(30) Foreign Application Priority Data

Nov. 5, 2001 (IN) .............................. 1127/DEL/01

(51) Int. Cl.
C12P 21/04 (2006.01)
(52) U.S. Cl. ................... 435/71.2; 435/71.1; 435/69.1; 530/350
(58) Field of Classification Search ............... 435/71.2, 435/71.1, 69.1, 252.33; 530/350
See application file for complete search history.

(56) References Cited

U.S. PATENT DOCUMENTS

| 5,800,821 | A * | 9/1998 | Acheson et al. ......... 424/200.1 |
| 6,602,712 | B2 * | 8/2003 | Handelsman et al. ....... 435/440 |
| 2002/0086032 | A1 * | 7/2002 | Mahan et al. ............. 424/200.1 |
| 2004/0076638 | A1 * | 4/2004 | Shiloach et al. .......... 424/190.1 |
| 2004/0148644 | A1 * | 7/2004 | Bier et al. ...................... 800/8 |
| 2005/0054038 | A1 * | 3/2005 | Bhatnagar et al. .......... 435/69.1 |

OTHER PUBLICATIONS

Chauhan, B e tal, Biochemical and Biophysical Research Communications, vol. 283, pp. 308-315, May 4, 2001, Constitutive Expression of Protective Antigen gene of *Bacillus anthracis* in *Escherichia coli*.*

Gupta, Pankaj et al, Protein Expression and Purificaton, 1999, vol. 16, pp. 369-376, Expression and Purification of the Recombinant Protective antigen of *Bacillus anthracis*.*

Ahuja, N et al, Rapid Purification of Recombinant Anthrax-Protective antigen under nondenaturing conditions, Biochemical and Biophysical Research Communications, vol. 286, pp. 6-11, 2001.*

Singh, Y et al, Infection and Immunity, vol. 66(7), Jul. 1998, pp. 3447-3448, Study of immunization against anthrax with the purified recombinant protective antigen of *Bacillus anthracis*.*

Farchaus, JW et al, Applied and Environmental Microbiology, Mar. 1998, vol. 64(3), pp. 982-991, Fermentation, Purification and characterization of protective antigen from a recombinant, avirulent strain of *Bacillus anthracis*.*

Miller, J et al, Letters in Applied Microbiology, 1998, pp. 56-60, vol. 26, Production and purification of recombinant protective antigen and protective efficacy against *Bacillus anthracis*.*

Iacono-Connors, LC et al, Clin and Diagn.c Lab. Immun., Jan. 1994, p. 78-82, vol. 1(1), Enzyme-linked immunosorbant assay using a recombinant baculovirus-expressed *Bacillus anthracis* protective antigen (PA): measurement of Human anti-PA antibodies.*

Difco 1996/97 Product Catalog for Microbiology, p. 176, Yeast Extract, carbohydrate % total being 17.5%.*

Janusz et al, (1986), Journal of Immunology, vol. 137(10), pp. 3270-3276,Nov. 15, 1986.*

Gupta, P et al, Biochemical and Biophysical Research Communications, Jul. 2001, vol. 285 (4). pp. 1025-1033, Enhanced expression fo the recombinant lethal factor of *Bacillys anthracis* by Fed-Batch culture.*

* cited by examiner

Primary Examiner—Jennifer Graser
Assistant Examiner—Kerima Maasho
(74) Attorney, Agent, or Firm—Ladas & Parry LLP

(57) ABSTRACT

The present invention relates to a process for preparing anthrax protective antigen protein from *E. coli* using fed batch culture. This process creates a constitutively expressing system for rapid, efficient, cost-effective and high-level production of anthrax PA from *E. coli*. The steps of the process involves, transforming *E. coli* DH5α cells with the recombinant constitutive expression plasmid containing the PA gene to obtain recombinant DH5α cells and testing the PA expression by lysis of said cells followed by denaturing gel electrophoresis and Western Blotting technique using PA antibodies. This is followed by fermentation and harvesting of the high cell density cells. The said cells are solubilized using 6-8 Molar Urea and separated by centrifugation. The urea denatured PA is isolated from said supernatant and purified and thereafter eluted.

13 Claims, 3 Drawing Sheets

Bacterial growth profiles depicting the effect of $MgSO_4$ on Batch cultures in fermentor

HIGH LEVEL CONSTITUTIVE PRODUCTION OF ANTHRAX PROTECTIVE ANTIGEN

FIELD OF THE INVENTION

This invention relates to high level constitutive production of anthrax protective antigen in *E. coli* by fed batch culture.

BACKGROUND OF THE INVENTION

Anthrax a zoonotic disease is caused by Gram positive, sporulating bacteria, *Bacillus anthracis*. Protective antigen, PA is the major component of all the vaccines against anthrax. Till date, culture supernatants of *B. anthracis* have been the major source of purifying PA. However, working with *B. anthracis* cultures requires P3 facilities that are cost-prohibitive. Apart from this, PA preparation from *B. anthracis* is often contaminated with other anthrax toxin proteins. Researchers have tried expressing and purifying PA in other microorganisms such as *Bacillus subtilis*, Baculovirus and *E. coli*. Purification of PA from *Bacillus subtilis* resulted in poor yields, required growth in rich media, and enormous amount of PA was degraded due to proteases secreted by the organism (L. W. J. Baillie et al, Lett. Appl. Microbial (1994) 19, 225-227). Baculovirus vectors expressed PA in insect cells; however, purification could not be possible due to low yields. Although PA has been expressed in *E. coli*, attempts to overproduce the protein were not successful (M. H. Vodkin et al, Cell, (1983) 34, 693-697). Researchers also purified PA by guiding the protein to the periplasmic spaces, however the yields of the purified PA were very low. All the known expression systems for Protective Antigen expression using *E. coli*, are inducible systems that require the use of IPTG, an expensive chemical.

U.S. Pat. No. 2,017,606 describes the preparation of anthrax antigen by growing *Bacillus anthracis* on a suitable culture medium and separating the *bacilli* from the culture medium.

U.S. Pat. No. 2,151,364 describes a method of producing an anthrax vaccine which comprises preparing the suspension of anthrax spores and adding to the suspension a sterile solution containing alum.

The drawbacks in the above US patents is that both of them use *Bacillus anthracis* cultures or spores. *Bacillus anthracis* is an infectious organism and cannot be handled without containment facilities. The levels of protective antigen expressed in *Bacillus anthracis* are very low. This kind of vaccine preparation is also contaminated with other toxic and non-toxic proteins from *Bacillus anthracis* resulting in a number of side-effects and reactogenicity.

The object of this invention is to create a constitutively expressing system for rapid, efficient, cost-effective and high-level production of anthrax PA from *E. coli* using Fed-Batch culture.

To achieve the said objective this invention provides a process for preparing anthrax protective antigen protein from *E. coli* using fed batch culture comprising:

transforming *E. coli* DH5α cells with the recombinant constitutive expression plasmid containing the PA gene to produce the recombinant DH5α cells expressing the PA protein, growing said recombinant DH5α cells and testing the PA expression by lysis of said cells followed by denaturing gel electrophoresis and Western Blotting technique using PA antibodies, fermenting said cells in a bio-reactor using:
polyols, carbohydrates or organic acids as primary supplements in Luria Broth medium at 32-42° C.,
fed-batch culture technique, and
pH-DO stat method of sensing nutrient deprivation to produce high cell density culture expressing PA protein, harvesting said cells by centrifugation of said high cell density culture at 5000-10,000 rpm for 10-30 minutes, solubilizing said high cell density culture cells by using 6-8 Molar Urea solution and stirring at ambient temperature for 1-2 hours, separating said high cell density culture debris by centrifugation at 10,000-15,000 rpm for 30-60 minutes at 32-42° C. and collecting the supernatant containing urea denatured PA, isolating said urea denatured PA from said supernatant and purifying it by Ni-NTA chromatography by gradual removal of urea while said PA is bound to the affinity column, and eluting said purified renatured PA and storing protective antigen (PA) protein as frozen aliquots at −20 to −70° C. depending upon immediate or long term use.

The said recombinant constitutive expression plasmid used expresses the PA protein as insoluble inclusion bodies in the *E. coli* strain DH5α cells.

The harvesting of said cells by centrifugation of said high cell density culture is carried out at 5000 rpm for 10 minutes.

The centrifugation of said high cell density culture debris is carried out at 10,000 rpm for 30 minutes for maximizing the harvesting of said cells.

The said polyol used as primary supplement in Luria Broth medium during fermentation is glycerol, The said carbohydrates used as primary supplement in Luria Broth medium are glucose, galactose, maltose, fructose and lactose, The said organic acid used as primary supplement in Luria Broth medium is malic acid.

By using polyol, carbohydrate or organic acid, as primary supplement in Luria Broth medium, the maximum cell density ranges between 10-14 optical density units in shake flask cultures.

The maximum cell density of the recombinant cells is achieved by Fed Batch cultures containing $MgSO_4$.

The concentration of Luria Broth medium used in the feed is 5-25×.

The concentration of Luria Broth medium used in the feed is 25× in order to minimize the volume of feed added during fermentation.

The said plasmid is pQE series vector containing an *E. coli* recognizable phage promotor.

An anthrax antigen comprises of purified structurally, biologically and functionally active recombinant protective antigen (PA) protein of *Bacillus anthracis* expressed as a 6× histidine fusion protein in *E. coli* DH5α cells free from polysaccharides, dead bacteria, culture medium, water-soluble and insoluble by-products and suspended impurities.

BRIEF DESCRIPTION OF THE DRAWINGS

The invention will now be described with reference to the following protocol and the accompanying drawings.

DETAILED DESCRIPTION

The recombinant constitutive expression plasmid containing the PA gene cloned in a pQE series vector was used for transforming *E. coli* strain DH5α competent cells. The said cells containing the recombinant plasmid were grown overnight at 37° C. and 250 rpm in Luria broth with 100 μg/ml of ampicillin. Cells were harvested by centrifugation at 5,000 rpm for 20 minutes. Expression and localization of PA was confirmed by SDS-PAGE. More than 90% of the recombinant protein was found to be present in inclusion bodies. The amount of protein expressed was found to increase in direct proportion to the increase in cell density of the growing culture.

Figure 1:
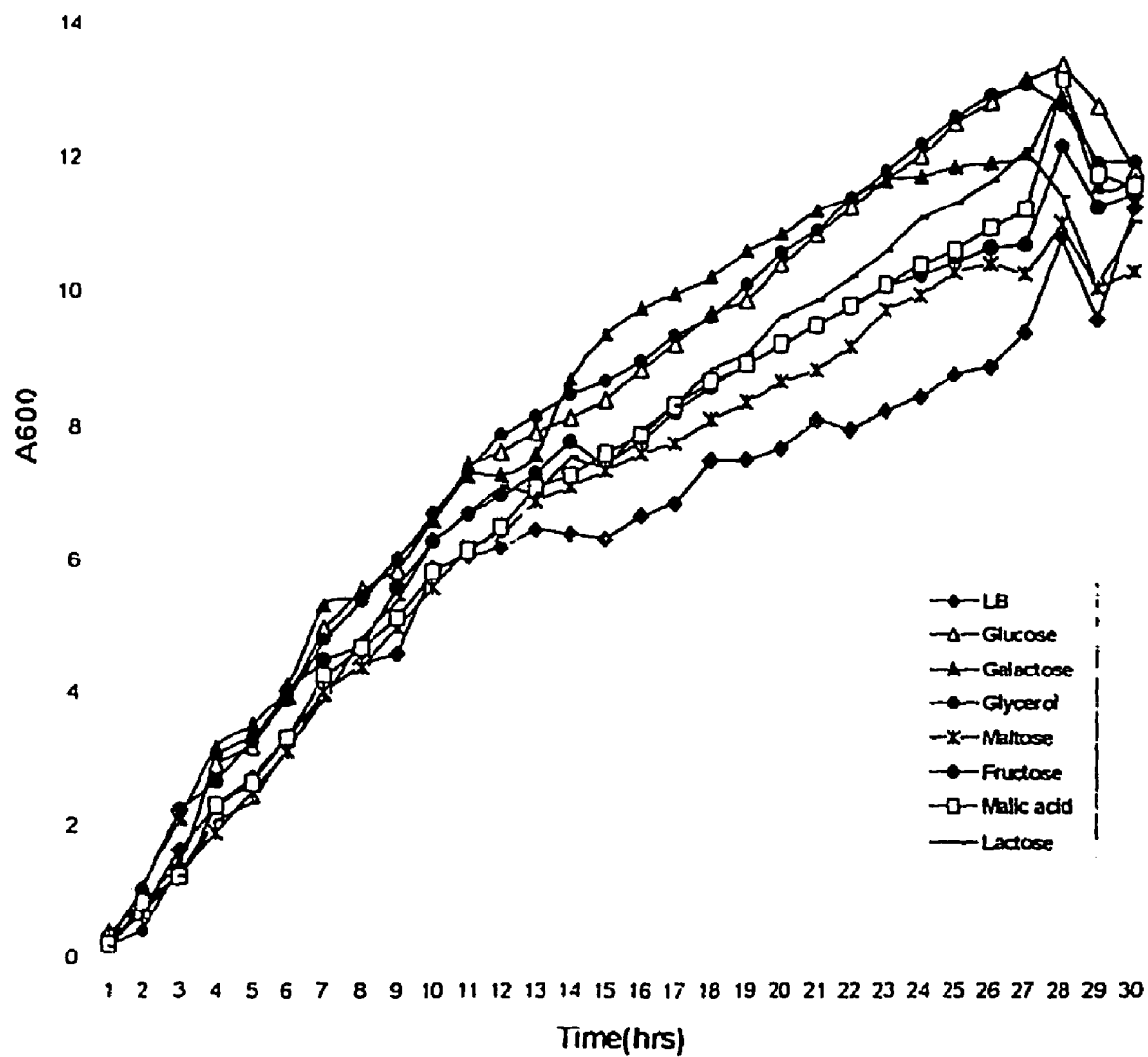
FIG. 1 shows that the maximum optical density in shake flask culture is obtained by using glucose as the additional carbon source and the minimum optical density is obtained by using maltose.

Complex media of modified 100 ml LB of 5× concentrations each was prepared with glucose, fructose, galactose, lactose, maltose, malic acid, and glycerol as seven different carbon sources in shake flasks. Only LB without any additional carbon source was used as a control. Equimolar amounts of carbon atoms were used as a carbon source and the concentration was kept equivalent to 0.5% glucose. 10 mM MgSO$_4$, 100 mM potassium phosphate and trace elements were also added. All the flasks were inoculated at the same time with an overnight grown inoculum of DH5α cells containing the said recombinant plasmid. Samples were collected aseptically every hour and OD$_{600}$ was measured. Culture aliquots were collected and their recombinant protein content was analyzed by SDS-PAGE. The highest OD$_{600}$ (Optical Density at 600 nanometers) could be achieved where glucose was used as the main carbon source and the lowest OD$_{600}$ was seen in the case of LB and maltose (FIG. 1). Maximum protein concentration was obtained by the use of malic acid, maltose and glycerol as the main carbon source. The lowest protein concentration was seen in the case of LB and lactose.

A 5 L Biostat B (B Braun Biotech International) fermentor equipped with pH, temperature, dissolved oxygen, and antifoam probes was used for the fermentation runs. The fermentor was interfaced with a personal computer. MFCS/win 2.0 software was used for data acquisition and operation of the fermentor in both batch as well as fed-batch mode.

The medium used for fermentation was a complex media consisting of Luria Broth with MgSO$_4$.7H$_2$O (10 mM), potassium phosphate (5 g/l) and glycerol (1%) at pH 7.4. For fed batch cultures, MgSO$_4$ was added to the medium before autoclaving. Glycerol was also added to the medium before autoclaving. A 25× feed was prepared with 25% glycerol (w/v) and 25× LB and autoclaved separately. Potassium phosphate solution was also autoclaved separately, allowed to reach the room temperature and added aseptically just before starting the run. The pH probe was calibrated with standard buffers of pH 7.0 and 9.2 before autoclaving. After autoclaving the fermentor media was automatically adjusted to pH7.4 by the addition of 1N NaOH/1 MHCl and temperature was set to 37° C. The DO (Dissolved oxygen) probe was calibrated by setting the electronic zero value of the dissolved oxygen in the range of zero to +15 nano-amperes (nAmp) and 100% DO value was given to oxygen tension of 2 vvm of pumped air, at an agitation rate of 250 rpm. The fermentor was started in batch phase with a working volume of 2 L. The recombinant plasmid containing cells were grown overnight on LB under the selective pressure of 100 μg/ml of ampicillin, at 37° C., 250 rpm. 1% of the overnight grown culture was used to inoculate the fermentor. The DO value was set at 40% and the stirrer was shifted to the cascade mode. In this mode, following the inoculation, as the DO begins to fall below 40%, the stirrer speed increases automatically to maintain the value at 40%. Samples were collected at an interval of 1 hour. The culture aliquots were diluted to an optical density (OD$_{600}$) approximately below 0.5 units. As the growing culture reached the mid log phase, feeding was started from the 25× feed using a peristaltic pump (Pharmacia). The feed rate was monitored and manually controlled to maintain a pH value between 7.2 and 7.4. Oxygen supplementation became necessary after an OD of 70 was reached. Oxygen was supplied to the culture by using the Gasmix function of the fermentor. The culture was grown to an OD$_{600}$ of 120 units after which the cells were harvested. Antifoam was initially added to the medium before autoclaving and later it was added as and when required.

Figure 2:
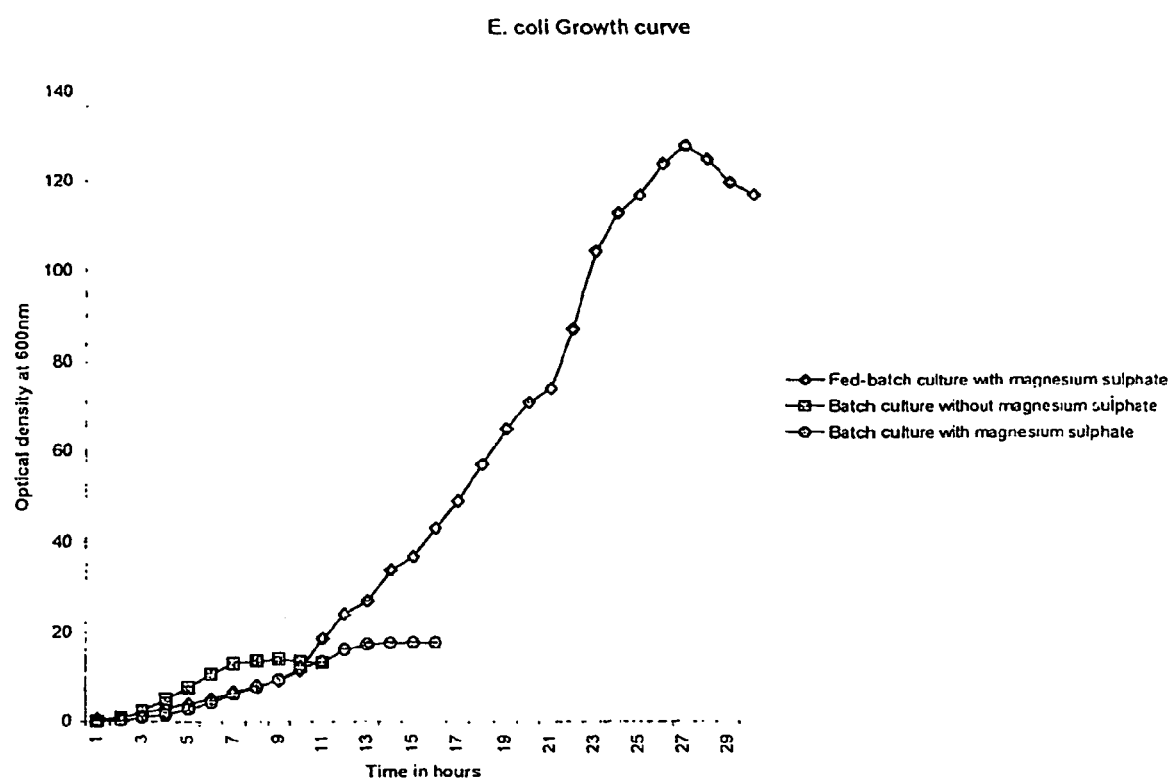
FIG. 2 shows that the optical density obtained in batch and Fed Batch cultures with and without the use of MgSO4.
Figure 3:
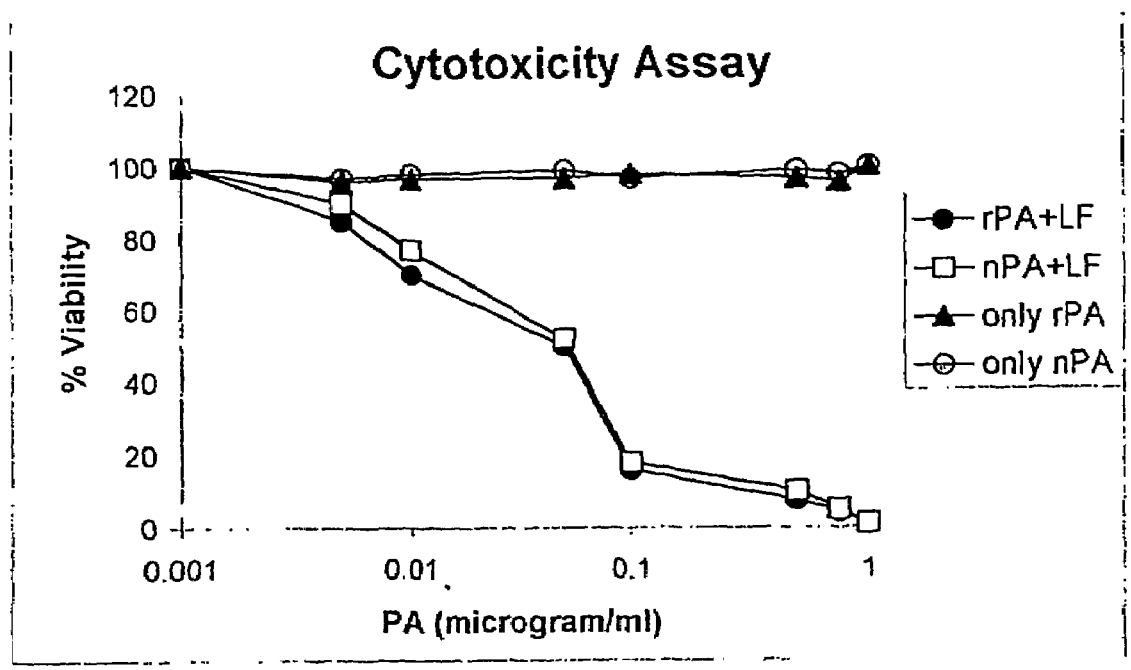
FIG. 3 shows that the recombinant PA produced is biologically and functionally as active as native PA from *Bacillus anthracis*.

To optimize the media composition and other conditions for the successive fermentation runs, a series of batch runs were carried out on modified LB with glycerol with or without the incorporation MgSO$_4$ in the growth medium. The batch runs without MgSO$_4$ in modified LB (with glycerol as carbon source) could attain the maximum OD of ~14 whereas the batch runs carried out with MgSO$_4$ in modified LB could attain OD$_{600}$ values of more than 18. It was inferred that MgSO$_4$ is necessary for the growth of cells at higher densities. The incorporation of MgSO$_4$ in the growth medium is essential for achieving higher biomass yields during fermentation. (FIG. 2).

5 ml of the high cell density culture was centrifuged at 10,000 g for half an hour in pre weighed tubes. After draining the supernatant, the tube with the centrifuged cells was weighed on a balance to determine the wet cell weight. To determine the dry cell weight, the same tube was left overnight in an incubator at 70° C. and was weighed next day.

To check the stability of the plasmid pMW1 in the fermentor, culture samples were aseptically collected every hour during the fermentation run. The samples were diluted such that the OD$_{600}$ of each sample was ~5.0 and centrifuged at 10,000 g for 1 minute. The supernatant was drained completely and the pellet was suspended in 100 μl lysis buffer containing 100 mM potassium phosphate buffer, pH8.0 with 8M urea. These samples were subjected to SDS-PAGE to check for the protein expression from the recombinant plasmid. Colony preparations and minipreparations of plasmid DNA were also made to directly check the presence of the recombinant plasmid inside the expressing cells. No noticeable generation of plasmid free cells was seen.

The protein was purified using metal-chelate affinity chromatography under denaturing conditions. In brief the pellet from 100 ml culture was resuspended in 100 ml of denaturing buffer containing 100 mM sodium phosphate buffer, 300 mM sodium chloride and 8M urea (pH 8.0). The resuspended pellet was incubated at 37° C. for 2 hrs. on a rotary shaker. The lysate was centrifuged twice for 60 min. each at room temperature and the supernatant was mixed with 50% Ni-NTA slurry. The slurry was packed into a column and allowed to settle. The, flow through was reloaded on the column. Ni-NTA matrix was washed with 500 ml denaturing buffer containing 8M urea, followed by on-column renaturation of the protein using 8M-0M Urea gradient. The protein was eluted with 250 mM Imidazole chloride in elution buffer, 100 mM sodium phosphate of pH 8.0 with 250 mM imidazole and 300 mM sodium chloride. 10 µl of each fraction was analyzed on 12% SDS-PAGE. Fractions containing the protein were collected, pooled and dialyzed against 10 mM HEPES buffer containing 50 mM NaCl and stored frozen at −70° C. in aliquots.

The specific protein was estimated by a number of methods. Densitometry was done using BioRad gel documentation system and the Quantity One software. The fold purification of PA was determined at different stages by calculating the amount of protein required to kill 50% of J774A.1 macrophage-like cells ($EC_{50}$) in combination with LF (1 µg/ml) for 3 hrs at 37° C. The purified protein was measured by Bradford's method and also by determining the OD of the preparation at 280 nm. PA accounted for more than 30% of the total cell protein and was present in the cells in the form of inclusion bodies. 5-8 g/L of PA was produced inside the cells.

The biological activity of the rPA (recombinant PA) was also determined by the cytotoxicity assay on J774A.1 macrophage like cell line. All experiments were done in triplicates. In brief varying concentrations of rPA protein alongwith LF (1 μg/ml) was added to the cells. The native PA from *B. anthracis* alongwith LF was kept as the positive control. After 3 hrs., cell viability was determined using MTT dye and the resulting precipitate was dissolved in a buffer containing 0.5% (w/v) sodium dodecyl sulfate, 25 mM HCl in 90% isopropyl alcohol. Absorption was read at 540 nm using a microplate reader (BioRad) and percent viability was determined. It was found that rPA alongwith LF was fully able to lyse macrophage cells and its biological activity was similar to PA prepared from *B. anthracis*. The $EC_{50}$ of rPA and nPA was found to be ~50 ng/ml each (FIG. 3) The fold purification of the protein was determined at each stage of purification by the above-mentioned cytotoxicity assays. (Table 1)

TABLE 1

Purification of PA from *Escherichia coli*

| Fraction | Volume (ml) | Protein (mg/ml) | Activity ($EC_{50}$)[a] | Purification (fold)[b] |
|---|---|---|---|---|
| Cell lysate | 10 | 291 | 57.3 | 1 |
| Affinity Purification | 25 | 1.8 | 0.0241 | 1965 |

[a]$EC_{50}$ is defined as the concentration of PA (μg/ml) along with LF (1 μg/ml) required to kill 50% of the J774A.1 cells. After 3 hrs. of incubation, viability was determined by MTT dye. The results represent the mean of three experiments.
[b]Purification fold was determined by dividing $EC_{50}$ for cell lysate with $EC_{50}$ for fractions obtained from different columns

DISCUSSION

The overexpression of any recombinant protein depends upon the optimum configuration of the various elements of the expression system. Several factors drastically affect recombinant protein expression like-promoter strength, plasmid stability, plasmid copy number, transcription terminators, transcription and translation efficiency that ultimately enhances mRNA stability, translation terminators, tight regulation of gene transcription, availability of ribosomes, post translational modifications, the stability and solubility of the recombinant protein itself, as well as host cell and culture conditions. Processes aiming at high levels of heterologous protein expression make use of strong promoters like T5, T7, PL, PR, Ptrc, Ptac, to create an effective expression system. Most of such systems carry inducible promoters and induction is preceded by a phase of low or no product formation. Upon induction, the specific production rate increases to a maximum within a short time period and the protein is continuously produced for 4-5 hours. Following induction, a number of changes have been reported like a change in carbon metabolism that results in acetate accumulation, an increase in respiratory activity, decrease in the synthesis of house keeping proteins, and occurrence of a heat shock-like response and SOS response. All of these responses contribute towards degradation of recombinant products. The formation of inclusion bodies prevents the recombinant protein from the onslaught of cellular proteases, which otherwise may result in extensive degradation of the protein leading to low product recoveries. The SDS-PAGE and Western blot analysis at different time points, corroborates the fact that expression of PA from the recombinant plasmid pMW1 is not leaky and is proportional to the OD of the culture. With no significant degradation, most of the protein was present inside the cells in the form of inclusion bodies.

Once a strong expression system is created, the recombinant protein production in *E. coli* can be increased significantly by the use of high cell density culture employing different techniques. Cell concentrations of more than 50 g/l of dry weight can be routinely achieved to provide cost effective production of recombinant proteins. But high cell density cultures also have a few drawbacks such as substrate inhibition, limited oxygen transfer capacity, the formation of growth inhibitory by-products, and limited heat dissipation resulting in reduction in the mixing efficiency of the fermentor. A major challenge in the production of recombinant proteins at high cell density culture (HCDC) is the accumulation of acetate, a lipophilic agent that is detrimental to cell growth. The accumulation of acetate in the growth medium is reported to reduce recombinant protein production. A number of strategies have been developed to reduce acetate formation in fed batch culture like controlling the specific growth rate by limiting essential nutrients of media such as carbon or nitrogen source, varying growth conditions and *E. coli* strains. Since the primary goal of fermentation research is cost-effective production of recombinant products, it is important to develop a cultivation method that allows the maximization of the yields of the desired product. The composition of the growth media is crucial for enhancing product formation as well as acetate reduction. Acetate is produced in *E. coli* under oxygen limiting conditions or in presence of excessive glucose under aerobic conditions, when carbon flux in the central metabolic pathway exceeds its biosynthetic demand and the capacity for energy generation within the cell.

On the basis of the growth kinetics and recombinant protein yields, glycerol was selected as the main carbon source for HCDC out of 7 other carbon sources namely, glucose, fructose, lactose, galactose, maltose, malic acid, and glycerol. Acetate is not produced when glycerol is used as a carbon source and high cell densities may be achieved relatively easily using glycerol. The lower rate of glycerol transport into the cell, compared with that of glucose, apparently leads to a reduction in the flux of carbon through glycolysis; greatly reducing acetate formation and the cells grow more slowly on glycerol. Glycerol also has an anti foaming effect that leads to less frothing during the course of the fermentation run.

The method utilized for nutrient feeding is also crucial for the success of HCDC as it affects both the cell density and cell productivity. Constant or intermittent feeding is carried out under nutrient limiting conditions. Although other feeding strategies have been successfully employed to HCDCs in E. coli, more sophisticated feeding strategies with feed-back control schemes have been developed lately. The feeding rate is coupled with other physical parameters such as DO (dissolved oxygen), pH microbial heat and $CO_2$ evolution rate (CER). The DO-stat method of feeding is based on the fact that the DO in the culture increases sharply when the substrate is depleted. The cells are not able to grow rapidly as the nutrient levels go down and lesser oxygen is utilized by the cells. Therefore, in the DC-stat method, the substrate concentration is maintained within the desired range by automatically adding a nutrient when the DO rises above the preset value. Another option, the pH-stat method is based on the fact that the media pH changes when the principal carbon source becomes limiting. When the carbon source is exhausted, the pH begins to rise mainly as a result of increase in the concentrations of ammonium ions excreted/secreted by the cells.

Analysis of the feeding system starts with characterization of the probing and detection method. The idea is to detect the saturation in the respiration by checking the DO and pH responses to pulses in the feed rate. Once feeding is initiated and E. coli enters into log phase, the feed is consumed more or less in an exponential manner. But, the feeding rate has to be controlled so that it doesn't exceed the nutrient demand or feed consumption rate. It is done by maintaining the pH and DO around their set values. A fall in pH and DO is an indication of substrate overdosing. Rise in pH and DO values indicate that the carbon source or one of the substrates is limiting and hence feed is required. If the increase in feed pulse/rate is unable to generate any significant response, i.e. fall in DO or increase in the stirrer speed, it is a perfect indication that some other factor like $MgSO_4$, $KH_2PO_4$ or trace elements has become limiting and has to be added intermittently on such occasions. The addition is followed by a rapid change in the above-mentioned variables. E. coli is able to utilize acetate as a carbon source when glucose or any other principal carbon source is absent. The consumption of acetate is characterized by a deviation from the preset values to lower pH values and cyclic patterns start appearing in the consumption of oxygen, till the preset pH value is gradually regained by the culture. At this time feeding is restarted.

The DO-stat method responds more rapidly to nutrient depletion than the pH-stat method. When complex substrates are used together with carbohydrate substrates, the DO change is not as apparent as the cells continue to use the complex substrates. The feeding strategy used in the present experiments was a combination of both the pH-stat as well as DO-stat methods. Monitoring of both the parameters simultaneously gives better control over the growth conditions of the growing culture. Making use of this strategy of substrate feeding we were able to achieve an OD of 120 which is a greater than six-fold increase from the OD achieved in the batch runs and more than 23-fold from that in the shake flask cultures.

This is the first report on optimization of fed-batch HCDC conditions to achieve high yields of PA in E. coli. This work is an attempt to obtain a large amount of non-reactogenic PA that could serve as a prospective vaccine candidate. The method of PA production reported here utilizes a novel and advantageous substrate and a simple and easy to control feeding strategy that may also be successfully applied to other recombinant protein expression systems to achieve high product yields.

The invention claimed is:

1. A process for preparing anthrax protective antigen protein from E. coli. using fed batch culture comprising the steps of
   (a) transforming E. coli DH5α cells with a recombinant constitutive expression plasmid containing the Protective Antigen gene to produce recombinant DH5α cells expressing the Protective Antigen protein,
   (b) growing said recombinant DH5α cells and testing Protective Antigen expression by lysis of said recombinant cells followed by denaturing gel electrophoresis and a Western Blotting technique using Protective Antigen antibodies,
   (c) fermenting said recombinant cells in a bio-reactor in Luria Broth medium at 32-42° C. in a fed batch culture, wherein the medium comprises nutrients, including a primary supplement selected from any one or all of a polyol, a carbohydrate and an organic acid, and wherein the fermenting comprises simultaneously monitoring a dissolved oxygen concentration and pH of the medium and, as nutrients are depleted from the medium, adding replacement nutrients to the medium to maintain the dissolved oxygen concentration and pH at levels that result in attainment of a high cell density culture that expresses Protective Antigen in a yield of at least 5 g/l,
   (d) harvesting said fermented cells by centrifugation of said high cell density culture at 5000-10,000 rpm for 10-30 minutes,
   (e) solubilizing said high cell density culture cells by using 6-8 Molar Urea solution and stirring at ambient temperature for 1-2 hours,
   (f) separating high cell density culture debris by centrifugation at 10,000-15,000 rpm for 30-60 minutes at 32-42° C. and collecting supernatant containing urea denatured Protective Antigen,
   (g) isolating said urea denatured Protective Antigen from said supernatant and purifying it by NI-NTA chromatography by gradual removal of urea with said Protective Antigen bound to an affinity column whereby to form purified renatured Protective Antigen, and
   (h) eluting the purified renatured Protective Antigen and, optionally, storing Protective Antigen protein as frozen aliquots at −20 to −70° C.

2. A process as claimed in claim 1, wherein said recombinant constitutive expression plasmid expresses the Protective Antigen protein as insoluble inclusion bodies in the E. coli strain DH5α cells.

3. A process as claimed in claim 1, wherein harvesting of said cells by centrifugation of said high cell density culture is carried out at 5000 rpm for 10 minutes.

4. A process as claimed in claim 1, wherein centrifugation of said high cell density culture debris is carried out at 10,000 rpm for 30 minutes for maximizing the harvesting of said cells.

5. A process as claimed in claim 1, wherein said polyol used during fermentation is glycerol, as primary supplement in Luria Broth medium at 37° C.

6. A process as claimed in claim 1, wherein said carbohydrate is selected from the group consisting of glucose, galactose, maltose, fructose, and lactose, as primary supplement in Luria Broth medium at 37° C.

7. A process as claimed in claim 1, wherein said organic acid is malic acid, as primary supplement in Luria Broth medium at 37° C.

8. A process as claimed in claim 1, wherein by using polyol, carbohydrate or organic acid, as primary supplement in Luria Broth medium, the maximum cell density ranges between 10-14 optical density units in shake flask cultures.

9. A process as claimed in claim 1, wherein the maximum cell density of the recombinant cells is achieved by a Fed Batch culture containing $MgSO_4$.

10. A process as claimed in claim 1, wherein the Luria Broth medium is fed into the bioreactor at 5-25 times dilution concentration of from an initial concentration of the Luria Broth medium.

11. A process as claimed in claim 1, wherein the Luria Broth medium is fed into the bioreactor at 25 times dilution concentration of 25X from an initial concentration of the Luria Broth medium.

12. A process as claimed in claim 1, wherein said plasmid is pQE series vector containing an *E. coli* recognizable phage promotor.

13. The process as claimed in claim 1, wherein the process consists essentially of said steps (a)-(h).

\* \* \* \* \*